US 6,697,677 B2
Feb. 24, 2004

(12) United States Patent
Dahl et al.

(54) SYSTEM AND METHOD FOR PLACING A MEDICAL ELECTRICAL LEAD

(75) Inventors: Roger Dahl, Andover, MN (US); Brad D. Pedersen, Minneapolis, MN (US); Duane Zytkovicz, Ham Lake, MN (US); Kenneth C. Gardeski, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 30 days.

(21) Appl. No.: 09/826,730

(22) Filed: Apr. 5, 2001

(65) Prior Publication Data

US 2002/0147484 A1 Oct. 10, 2002

Related U.S. Application Data

(60) Provisional application No. 60/258,683, filed on Dec. 28, 2000.

(51) Int. Cl.[7] .................................................. A61N 1/05
(52) U.S. Cl. ....................... 607/128; 606/129; 607/119
(58) Field of Search ............................. 600/372–381, 600/505; 607/122–132, 116, 119

(56) References Cited

U.S. PATENT DOCUMENTS

| | | | |
|---|---|---|---|
| 4,585,013 A | | 4/1986 | Harris |
| 5,071,407 A | * | 12/1991 | Termin et al. ............. 604/104 |
| 5,087,244 A | | 2/1992 | Wolinsky et al. |
| 5,228,455 A | * | 7/1993 | Barcel ........................ 607/127 |
| 5,246,014 A | | 9/1993 | Williams et al. |
| 5,282,845 A | | 2/1994 | Bush et al. |
| 5,545,149 A | | 8/1996 | Brin et al. |
| 5,639,276 A | | 6/1997 | Weinstock et al. |
| 5,755,704 A | | 5/1998 | Lunn |

(List continued on next page.)

FOREIGN PATENT DOCUMENTS

| | | |
|---|---|---|
| EP | 0 601 338 B1 | 6/1994 |
| WO | WO 98/32375 | 7/1998 |
| WO | WO 98/43697 | 10/1998 |

Primary Examiner—George R. Evanisko
(74) Attorney, Agent, or Firm—Michael C. Soldner; Girma Wolde-Michael

(57) ABSTRACT

An improved system and method that is capable of delivering multiple electrode assemblies to predetermined implant sites within a body is disclosed. The system includes an elongated member such as an introducer sheath. The introducer includes an elongated channel along at least a distal end portion of the introducer. The elongated channel opens to the exterior surface of the introducer through an elongated slot. One or more electrode assemblies may be retained within the elongated channel such that the leads exit the introducer via the elongated slot. The elongated introducer further includes a lumen that is in fluid communication with channel through openings, or gaps. The electrode assemblies are loaded within the channel at predetermined positions with respect to the openings. A distal end of a stiffening member such as a stylet may then be advanced within the lumen and through a selected one of the openings to engage an electrode assembly. The distal end of the stylet, along with the electrode assembly, is pushed in a distal direction within the channel until the electrode assembly exits the channel at a predetermined implant site. The stylet is then de-coupled from the electrode assembly, and the distal end is again retracted into the lumen. The distal end of the stiffening member may be re-directed into a different opening to engage a second electrode assembly. After the introducer is repositioned at a second implant site, the second electrode assembly may be deployed in a manner similar to that discussed above. The process may be repeated to deploy an array of electrodes. According to one aspect of the invention, the stylet distal end is canted to extend from the lumen of the introducer into the channel.

24 Claims, 15 Drawing Sheets

U.S. PATENT DOCUMENTS

| | | | |
|---|---|---|---|
| 5,769,881 A | * | 6/1998 | Schroeppel et al. ........ 607/123 |
| 5,782,898 A | | 7/1998 | Dahl et al. |
| 5,803,928 A | * | 9/1998 | Tockman et al. ........... 607/122 |
| 5,811,043 A | | 9/1998 | Horrigan et al. |
| 5,851,226 A | | 12/1998 | Skubitz et al. |
| 5,902,331 A | | 5/1999 | Bonner et al. |
| 6,006,137 A | | 12/1999 | Williams |
| 6,094,596 A | | 7/2000 | Morgan |

* cited by examiner

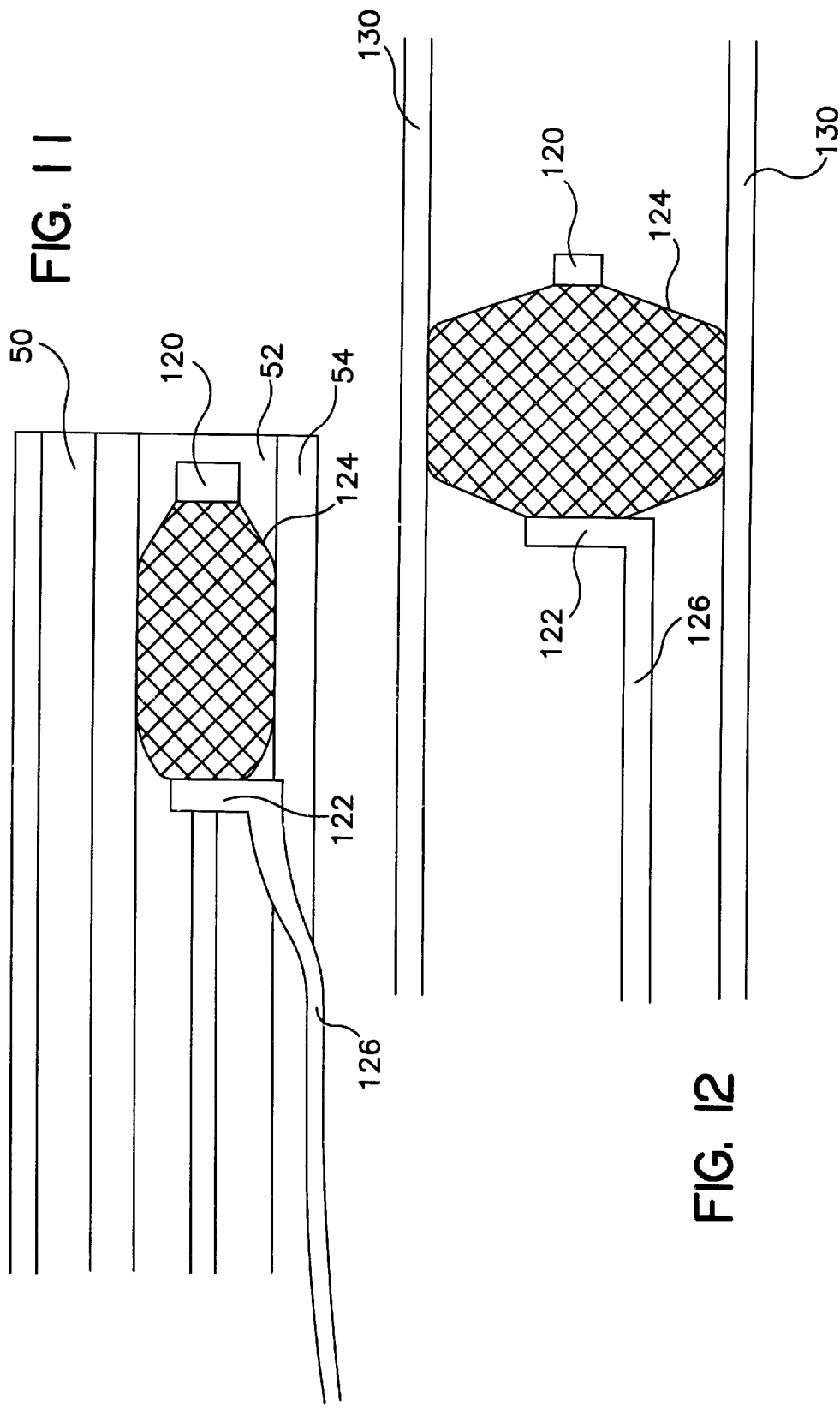

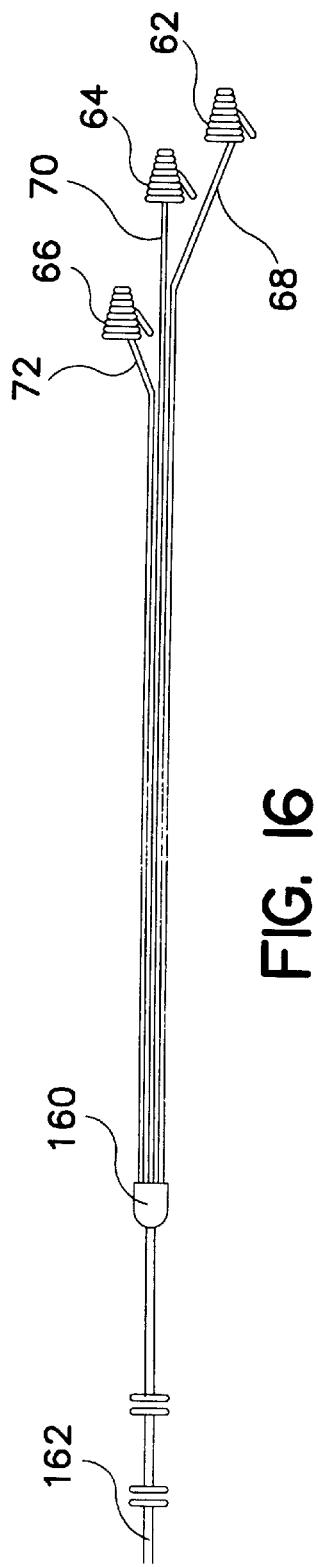

SYSTEM AND METHOD FOR PLACING A MEDICAL ELECTRICAL LEAD

RELATED APPLICATIONS

This application claims priority to provisionally-filed U.S. Patent Application Serial No. 60/258,683 filed Dec. 28, 2000 entitled "System and Method for Placing a Medical Electrical Lead", which is incorporated herein by reference in its entirety.

FIELD OF THE INVENTION

The present invention relates generally to a system and method for placing one or more implantable cardiac leads within a coronary artery or cardiac vein; and more particularly, relates to a system and method that may be used to implant an electrode array within one or more vessels of a body using a single-pass procedure.

BACKGROUND OF THE INVENTION

Implantable medical electrical stimulation and/or sensing leads are well known in the fields of cardiac stimulation and monitoring, including cardiac pacing and cardioversion/defibrillation. In the field of cardiac stimulation and monitoring, endocardial leads are placed through a transvenous route to locate one or more sensing and/or stimulation electrodes along, or at the distal end of, the lead in a desired location within a heart chamber or interconnecting vasculature. In order to achieve reliable sensing of the cardiac electrogram and/or to apply stimulation that effectively paces or cardioverts the heart chamber, it is necessary to accurately position the electrode surface against the endocardium or within the myocardium at the desired site and fix it during an acute post-operative phase until fibrous tissue growth occurs.

The pacemaker or defibrillator implantable pulse generator (IPG) or the monitor is typically coupled to the heart through one or more of such endocardial leads. The proximal end of such a lead is typically formed with a connector that connects to a terminal of the IPG or monitor. The lead body typically comprises one or more insulated conductive wires surrounded by an insulating outer sleeve. Each conductive wire couples a proximal lead connector element with a distal stimulation and/or sensing electrode.

In order to implant an endocardial lead within a heart chamber, a transvenous approach is utilized wherein the lead is inserted into and passed through the subclavian, jugular, or cephalic vein and through the superior vena cava into the right atrium or ventricle. An active or passive fixation mechanism is incorporated into the distal end of the endocardial lead and deployed to maintain the distal end electrode in contact with the endocardium position.

More recently, endocardial pacing and cardioversion/defibrillation leads have been developed that are adapted to be advanced into the coronary sinus and coronary veins branching therefrom in order to locate the distal electrode(s) adjacent to the left ventricle or the left atrium. The distal end of such coronary sinus leads is advanced through the superior vena cava, the right atrium, the valve of the coronary sinus, the coronary sinus, and may further be advanced into a coronary vein communicating with the coronary sinus, such as the great vein. Typically, coronary sinus leads do not employ any fixation mechanism and instead rely on the close confinement within these vessels to maintain each electrode at a desired site.

Routing an endocardial lead along a desired path to implant the electrode or electrodes in a desired implantation site, either in a chamber of the heart or in the selected cardiac vein or coronary artery, can be difficult. This is particularly true for steering leads through the coronary sinus and into a branching vein on the left myocardium. Anomalies in the vascular anatomy and the number of branch veins associated with the anatomy make locating the desired path challenging.

Several common approaches have been developed to place electrodes within the vascular system of the heart. According to one approach, a guide catheter is steered into the desired location in the vasculature. A lead is then fed through the inner lumen of the catheter such that the lead electrode(s) are positioned at predetermined locations. The guide catheter may then be withdrawn. This type of approach is described in commonly assigned U.S. Pat. Nos. 6,006,137, 5,246,014, and 5,851,226 incorporated herein by reference. The described systems employ highly flexible, catheters surrounding the lead body. One difficulty with systems of this nature is that the lead body may not be pushable and trackable enough to be advanced through the catheter lumen. This is particularly true when the catheter is positioned within the torturous curves of a patient's vasculature system. The problem is exaggerated when very small leads having a diameter of 4 French or less are employed for use in the coronary sinus or associated vasculature.

Another approach to lead placement involves the use of a guide wire that is steered into a desired location within the vasculature. The lead body is then tracked over the wire and the wire is withdrawn. According to this design, the guide wire passes through an inner lumen of the lead for an entire length of the lead. This results in a significant amount of friction that can make lead placement difficult. Additionally, since the lead must include an inner lumen for the guide wire, the size of the lead is at least somewhat dictated by the size of the guide wire. Moreover, to accomplish lead placement in this manner, the lead must again be both pushable and trackable enough to allow it to be advanced over the guide wire through the tortuous curves of the vasculature.

Yet another approach is described in commonly-assigned U.S. Pat. No. 5,902,331 to Bonner et al. The disclosed system includes a pusher mechanism that is adapted to slidably engage a guidewire that has previously been placed at a desired implant site. The pusher mechanism couples to a lead body to allow the pusher to guide the lead over the guidewire to the desired implant site. The lead body may then be released from the pusher, and the pusher and guidewire are withdrawn from the body.

One problem with the system and method disclosed in the '331 patent discussed above is that the system is not adapted to efficiently delivery multiple leads. To deliver more than a single lead using a system with a pusher mechanism involves withdrawing the pusher from the body, loading an additional lead on the guidewire, and deploying the lead from the guidewire in the manner discussed above. Because the pusher must be withdrawn from the body each time an additional lead is loaded onto the guidewire, the time of implant is significantly increased. Additional handling of the guidewire outside the body also increases the risk of infection. Moreover, the position of the distal tip of the guidewire must be moved to a new implant site before any additional lead is delivered, increasing the variability associated with the selected site of implant.

The use of multiple-lead electrode arrays is particularly desirable in the delivery defibrillation and cardioversion therapies. For example, by placing multiple, spaced apart defibrillation electrodes within the coronary sinus or a branch vein such as the Middle Cardiac Vein (MCV), the defibrillation threshold can be reduced as compared to a system using a single electrode for the delivery of electrical stimulation.

What is needed, therefore, is an improved system and method for placing leads within coronary arteries and cardiac veins such as the Middle Cardiac Vein (MCV) that is readily adapted for placing multiple leads at respective predetermined implant sites.

SUMMARY OF THE INVENTION

An improved system and method that is capable of delivering multiple electrode assemblies to predetermined implant sites within a body is disclosed. The system includes an elongated tubular member such as an introducer sheath. The introducer includes an elongated channel along at least a distal end portion of the introducer. The elongated channel opens to the exterior surface of the introducer through an elongated slot. One or more electrode assemblies may be retained within the elongated channel such that the leads coupled to the electrode assemblies exit the introducer via the elongated slot.

The elongated introducer further includes a lumen that is in fluid communication with the channel through openings, or gaps, between the lumen and the channel. The electrode assemblies are loaded within the channel at predetermined positions with respect to the openings. A distal end of a stiffening member such as a stylet may then be advanced within the lumen, inserted through a selected opening to enter the channel, and coupled to an associated electrode assembly. The stiffening member is further advanced within the channel to push the electrode assembly from the distal end of the channel at a predetermined implant site. The lead coupled to the electrode assembly is allowed to trail the electrode assembly through the slot as the electrode assembly is deployed.

To deploy any additional electrode assemblies, the stiffening member is retracted until the distal end of the stiffening member is again located within the lumen. The introducer may then be re-positioned at a second implant site, which is preferably located at a proximal position within a vessel as compared to the first implant site. The stiffening member distal end is again positioned through a different one of the openings to engage a second electrode assembly. The second electrode assembly is deployed in a manner similar to that discussed above. Additional electrode assemblies may be deployed in a similar manner. Thus the inventive system and method allows an array of electrodes to be positioned within one or more vessels within a body without having to withdraw an introducer or a stiffening member from the body during the implant procedure to re-load additional electrodes.

According to one aspect of the invention, the stiffening member may include a cant, or bend, at the distal end. This cant is adapted to readily allow the distal end of the stiffening member to extend from the lumen into the channel. The stiffening member is preferably formed of a material such as a superelastic alloy that may be deformed without losing an original pre-formed shape. This allows the stiffening member to flex as the body of the stiffening member is advanced through a selected opening from the lumen to the channel as an electrode is deployed.

In one embodiment, the proximal end of stiffening member includes one or more markers to aid a user in locating the openings of the lumen prior to electrode deployment. For example, in one embodiment, the markers are visible indicators at a proximal end of a stylet that may be aligned so that distal end of the stylet is adjacent a selected opening. Alternatively, a handle coupled to introducer could include a travel limiter that engages a protrusion in the stiffening member to indicate when alignment has occurred.

Many different types of electrode assemblies may be adapted for use with the current invention. In one embodiment, the electrode assemblies are self-expanding electrodes that include fixation means that expand to contact one or more walls of a vessel. This allows the electrode assembly to be retained at a predetermined site of implant until tissue in-growth begins.

The electrode assemblies of the current invention further include a mechanism for engaging the stiffening member. For example, the electrode assembly may include an inner lumen to receive the distal end of the stiffening member. The inner lumen may include a key to engage a keyed structure of the stiffening member. According to one embodiment, the key may be adapted to receive the distal end of a bladed stylet assembly.

As described above, the stiffening member is coupled to the electrode assembly prior to deploying the electrode assembly. The stiffening member may then be advanced in a distal direction to cause the electrode assembly to exit the channel of the introducer. In an embodiment in which the electrode assembly is self-expanding, the electrode assembly expands upon exiting the channel. When a proximal force is then applied to the stiffening member, the distal end of the introducer de-couples the electrode assembly from the stiffening member.

According to another aspect of the invention, the distal end of the introducer may include an inflatable collar that is in fluid communication with an inflation lumen. Using a port at the proximal end of the introducer, the inflatable collar may be expanded to retain the introducer at a predetermined location within a vessel during electrode deployment. The introducer may further include a second port that is capable of providing fluid to the channel carrying the electrode assemblies. For example, a saline drip may be coupled to the second port so that the channel remains lubricious during the implant procedure. This further aids in minimizing thrombus formations.

The inventive system may further include a sheath for binding the leads of the electrode assemblies together to minimize wear and also reduce tissue abrasion. The sheath may be formed of loosely braided fibers. The tube may be anchored to the distal end of the introducer with a tether such as may be formed of surgical suture material. After all electrode assemblies are placed, the proximal end of the tube is tightened to hold the leads snug. A weakened spot in the tether may be provided to allow the tether to be de-coupled from the introducer upon application of adequate tension. This allows the flexible tube to remain in place around the leads after the introducer is withdrawn from the body.

Other scopes and aspects of the current invention will become apparent to those skilled in the art from the accompanying detailed description and the drawings.

BRIEF DESCRIPTION OF THE DRAWINGS

FIG. 11 is a plan view of yet another embodiment of a self-expanding electrode assembly.

FIG. 12 is a plan view of the electrode assembly embodiment of FIG. 11 within a vessel after the electrode has been deployed.

FIG. 16 is a plan view illustrating one embodiment of electrode assemblies interconnected to a single connector pin.

DETAILED DESCRIPTIONS OF THE DRAWINGS

Figure 1:
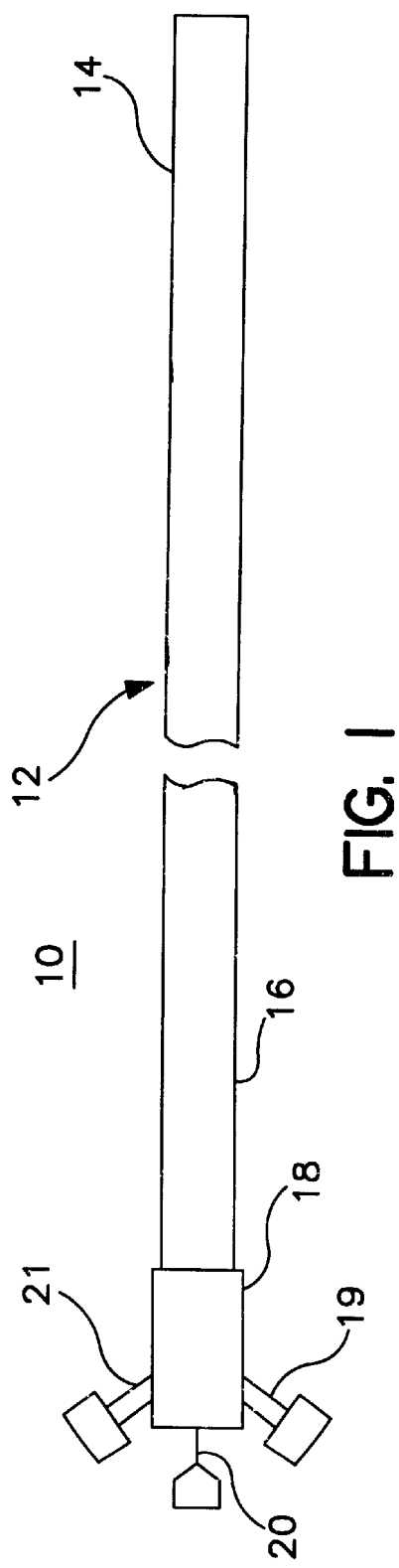
FIG. 1 is a plan view illustrating a lead delivery system for delivering multiple leads to a predetermined site of implant according to the current invention.

FIG. 1 is a plan view illustrating a lead delivery system for delivering multiple leads to a predetermined site of implant according to the current invention. Lead delivery system 10 includes an elongated tubular member such as an introducer 12 having a distal end 14 and a proximal end 16 coupled to a handle structure 18. Handle structure may include one or more side arms 19 and 21, each with a port to receive a syringe. One or more of the ports provided by side arms 19 and 21 may include a luer lock fitting, as is described further below. Introducer 12 may be formed of silicone rubber or thermoplastic polymers such as polyurethane, polyethylene, polyester, polyamide or any other biostable, biocompatible polymer known in the art. Handle structure 18 is adapted to receive a stiffening member 20 such as a stylet.

Figure 2:
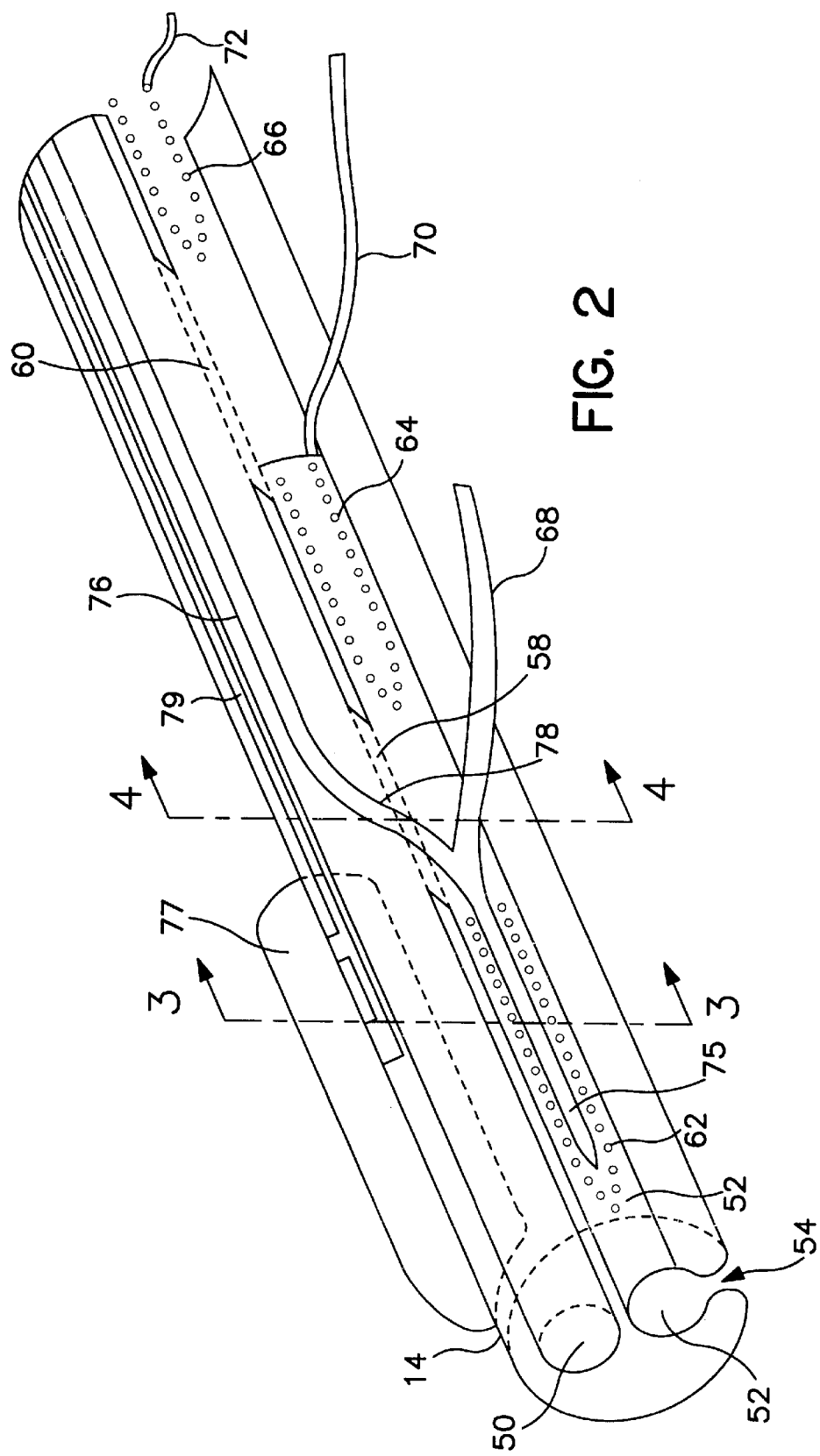
FIG. 2 is a side perspective cutaway view of distal end of the introducer.

FIG. 2 is a side perspective cutaway view of distal end 14 of introducer 12. Introducer includes a lumen 50 extending to the proximal end of the introducer. The introducer further includes a channel 52 that takes the form of a "C" shaped lumen having a longitudinal slot 54 that opens to the exterior surface of introducer. Channel 52 and slot 54 may extend to proximal end 16 of introducer 12, or alternatively, may only extend along the length of distal end 14 of the introducer. At predetermined locations along the distal end 14 of introducer 12, interconnecting openings join lumen 50 to channel 52. For example, openings are shown as gaps 58 and 60 in FIG. 2, although as few as one, or more than two, gaps could be provided according to the current invention.

Although channel 52 is shown being continuous between the loaded electrode assemblies, it will be understood channel 52 may be interrupted, or "filled in", at certain locations between the cutaway portions provided to receive electrode assemblies. In this alternative embodiment, channel 52 may be described as multiple, longitudinally-aligned channels, each in fluid communication in at least one location with lumen 50, and each to receive a respective electrode assembly.

Channel 52 is adapted to receive one or more electrode assemblies shown as electrode assemblies 62, 64, and 66. Each electrode assembly is shown coupled to a respective lead body 68, 70, and 72. Each lead body carries a conductor that couples the respective electrode assembly to the proximal end of the respective lead body, as will be discussed further below. Lead bodies 68, 70, and 72 extend through slot 54 of channel 52, and are located adjacent introducer 12 during the implant procedure as will be discussed further below.

As discussed above, lumen 50 is adapted to receive a stiffening member 20 such as a stylet. Lumen 50 may be coated with a lubricious material such as PTFE or ETFE to facilitate passage of the stiffening member 20. In FIG. 2, stiffening member 20 is shown as a stylet 76 having a canted portion 78. During use, distal end of stylet is inserted into lumen 50 at the proximal end 16 of introducer via handle 18. The distal end of stylet 76 is advanced to the distal end 14 of introducer 12 in a manner to be discussed below. When advanced to a predetermined location, canted portion 78 is designed to extend between lumen 50, through one of the gaps shown as gaps 58 and 60, and into channel 52. Distal end 75 of stylet 76 then engages with a selected one of the electrode assemblies in a manner to be discussed below. FIG. 2 illustrates stylet 76 engaging electrode assembly 62.

In one embodiment of the invention, distal end 14 of introducer 12 may include an inflatable member 77 such as a balloon. The inflatable member may be formed of compliant or non-compliant polymer materials. Example of materials that are suitable for construction of such a structure include polyurethane, polyamide, PET, and latex. In one embodiment, the inflatable member is formed of Pellethane® thermoplastic polyurethane having a stiffness of approximately 80A Shore, which is commercially available from the Dow Chemical Company. In yet another embodiment, the inflatable member may be constructed of a material that is permeable, or that has micro-pores to allow the fluid from within the inflatable member to slowly seep to the exterior of the balloon. A "weeping" balloon of this type is described in U.S. Pat. No. 5,087,244 to Wolinsky et al. which is incorporated by reference in its entirety. In one embodiment, the balloon has an inflated diameter of between approximately 1.5 to 4 mm, and a length of between approximately 10 to 40 mm. The balloon may be attached to the introducer 12 using a thermal or adhesive, as is known in the art.

Inflatable member 77 is fluidly coupled to an inflation lumen 79. A syringe inserted in side arm 19 (FIG. 1) may inject fluid into inflation lumen 79 to expand inflatable member to a size that temporarily occludes a vessel such as the coronary sinus in which introducer 12 is placed. This maintains introducer 12 at a desired location of implant during electrode deployment. Inflatable member may be fully or partially deflated by withdrawing fluid via the inflation lumen 79 so that the inventive system may be re-positioned, or withdrawn from the body.

According to another aspect of the current invention, channel 52 is in fluid communication with a port in side arm 21. Side arm includes a luer lock fitting adapted to allow a saline drip to continuously flush through channel 52. This minimizes thrombus formation up to the proximal end of slot 54 and increases the ease with which the electrode assemblies are deployed.

Figure 3:
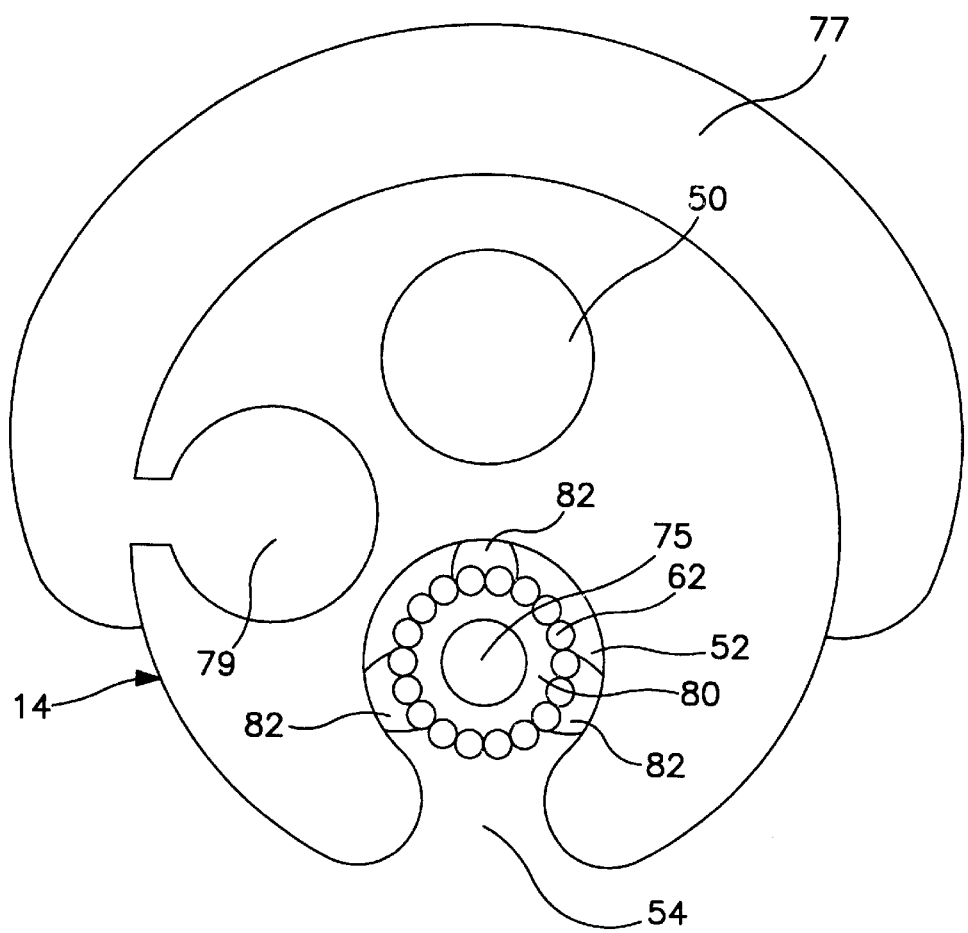
FIG. 3 is a cross-sectional view of the introducer at line 3—3 of FIG. 2.

FIG. 3 is a cross-sectional view of introducer 12 at line 3—3 of FIG. 2. This view shows electrode assembly 62 residing within channel 52. Electrode assembly includes a lumen 80 that engages distal end 75 of stylet 76. The embodiment of electrode assembly shown in FIG. 3 also includes expandable member 82, which expand when the electrode assembly is deployed to maintain the electrode assembly at a predetermined implant site. This is discussed in detail below.

FIG. 3 further shows inflatable member 77 coupled to inflation lumen 79, which is provided in one embodiment of the invention to stabilize introducer 12 at a desired site of implant. Inflatable member 77 is formed to surround only a portion of introducer 12, leaving slot 54 open for lead deployment.

As discussed above, channel 52 extends to the exterior of introducer 12 via slot 54. Also shown in FIG. 3 is lumen 50 adapted to receive stylet 76 (not shown in FIG. 3.)

Figure 4:
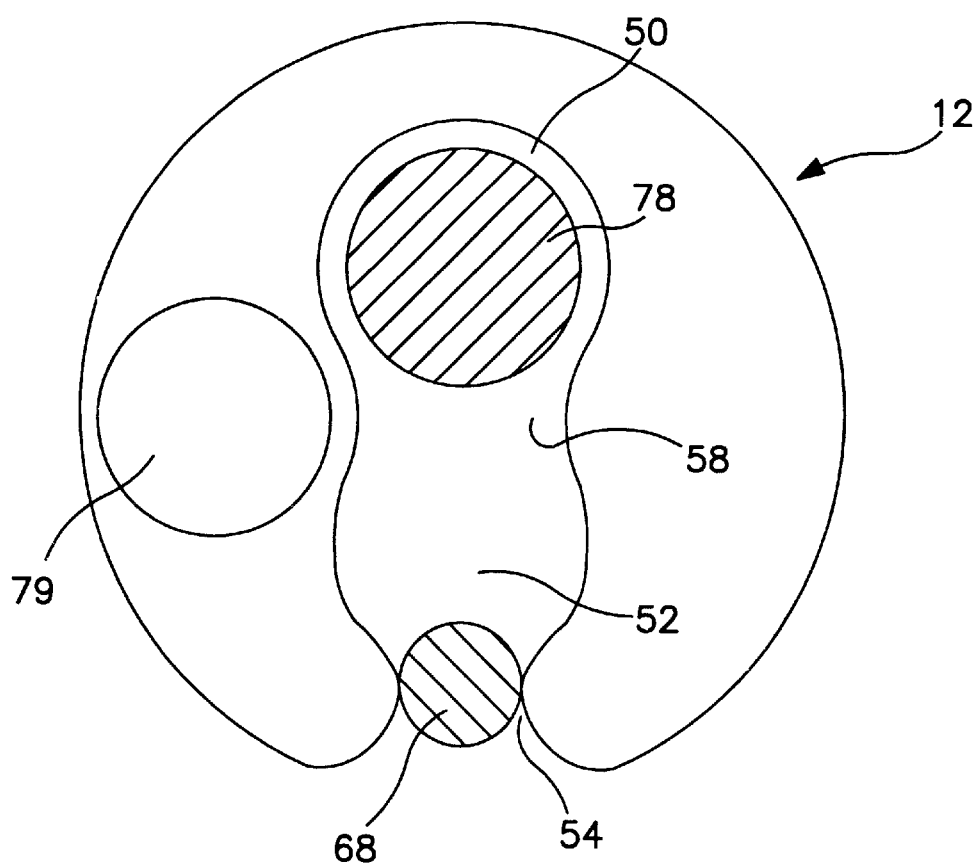
FIG. 4 is a cross-sectional view of the introducer at line 4—4 of FIG. 2.

FIG. 4 is a cross-sectional view of introducer 12 at line 4—4 of FIG. 2. This view shows lumen 50 extending to channel 52 via gap 58. This view further illustrates an oblique view of canted portion 78 of stylet 76 located within gap 58, and lead body 68 occupying slot 54 in the manner discussed above.

Figure 5:
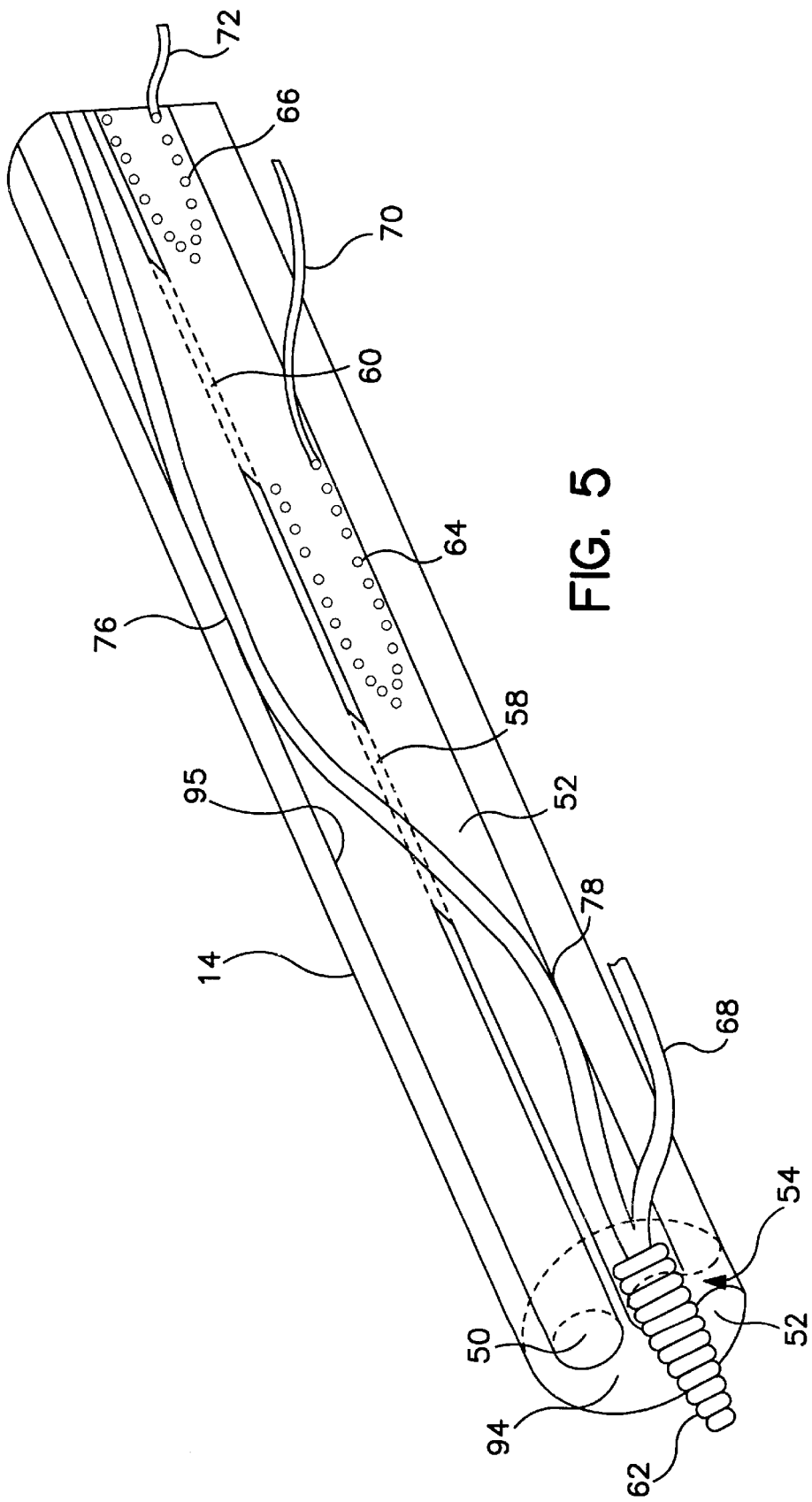
FIG. 5 is a side perspective cutaway view showing the manner in which introducer and stylet are used to deploy an electrode assembly.

FIG. 5 is a side perspective cutaway view showing the manner in which introducer 12 and stylet 76 are used to deploy an electrode assembly. As discussed above in reference to FIG. 2, distal end 75 of stylet engages electrode assembly 62 in a manner to be discussed further below. Stylet is then slid distally such that canted portion of the stylet is completely located within channel 52. Sliding stylet distally pushes electrode assembly 62 distally within channel 52. Deployment of the electrode may be further aided by coating lumen 52 and slot 54 with a lubricious material such as PTFE or ETFE. This distal motion of stylet eventually results in the electrode assembly 62 exiting the distal end of channel 52, as shown in FIG. 5. The respective lead body 68 coupled to electrode assembly 62 is allowed to exit to the exterior of introducer 12 via slot 54 during deployment of the electrode.

As discussed above, during electrode deployment, canted portion 78 of stylet enters channel 52. To allow this to occur without permanently deforming the stylet, stylet is formed of a flexible material such as a superelastic alloy which will resume the original shape when force is no longer asserted on the structure. For example, stylet could be formed of platinized Nitinol. Because of the flexibility of stylet, canted portion is substantially straightened within channel 52, whereas a region of the stylet 92 which is adjacent, and proximal to, canted portion 78 forms a bend because of tension formed when the stylet body transitions between lumen 50 to channel 52 via gap 58. As stated previously, region 92 of the stylet will resume a substantially straightened configuration when the tension is removed.

According to one embodiment of the invention, an expandable electrode assembly is used with introducer 12. The expandable electrode is compressed within channel 52 prior to deployment, but expands after the electrode assembly exits channel 52. This expansion results in an electrode assembly having a diameter that is larger than the diameter of channel 52. By asserting a force on the stylet 76 which urges the stylet in a proximal direction, the proximal end of the electrode assembly comes in contact with distal end surface 94 of introducer 12. This disengages the electrode assembly 62, pushing it off from stylet 76 so that it is deployed within the vessel at a desired implant site. The lead body 68 is also completely disengaged from introducer, and lies adjacent to the exterior surface of the introducer.

After the most distally-located electrode assembly 62 is deployed, the current inventive system and method may be utilized to deploy the electrode that remains at the next-most distal position within channel 52. To accomplish this, stylet 76 is retracted in a proximal direction so that canted region 78 re-enters gap 58 and is pulled into lumen 50. A marker mechanism located in handle 18 provides an indication that canted region 78 has entered lumen 50, as will be discussed further below. The user then rotates stylet 76 180 degrees so that canted region is urged against the outer-most wall 95 of lumen 50, causing the stylet to assume a substantially-straightened configuration. The user may then continue to pull the stylet 76 in the proximal direction until the marker mechanism again indicates that the stylet is in a predetermined position adjacent electrode assembly 64. The user then again rotates the stylet 76 180 degrees to allow canted region 78 to enter gap 60 so that distal tip 75 of stylet 76 may enter channel 52 to engage electrode assembly 64.

After stylet 76 engages electrode assembly 64, a force may be applied to the proximal end of introducer 12 to move the introducer and stylet a predetermined distance in a proximal direction to a second implant site. Then a force is again asserted on the proximal end of stylet 76 to urge the distal end of stylet in a forward direction within channel 52. This causes electrode assembly to move forward within the channel until it is deployed at the second implant site in a manner discussed above with respect to electrode assembly 62. Expansion of electrode assembly 64 in the manner discussed above allows the electrode assembly to be disengaged from stylet 76 by applying a force in the proximal direction on the stylet in the manner discussed above.

The foregoing process may be repeated to deploy electrode assembly 66, and any other electrode assemblies that may be pre-loaded within introducer 12.

Figure 6:
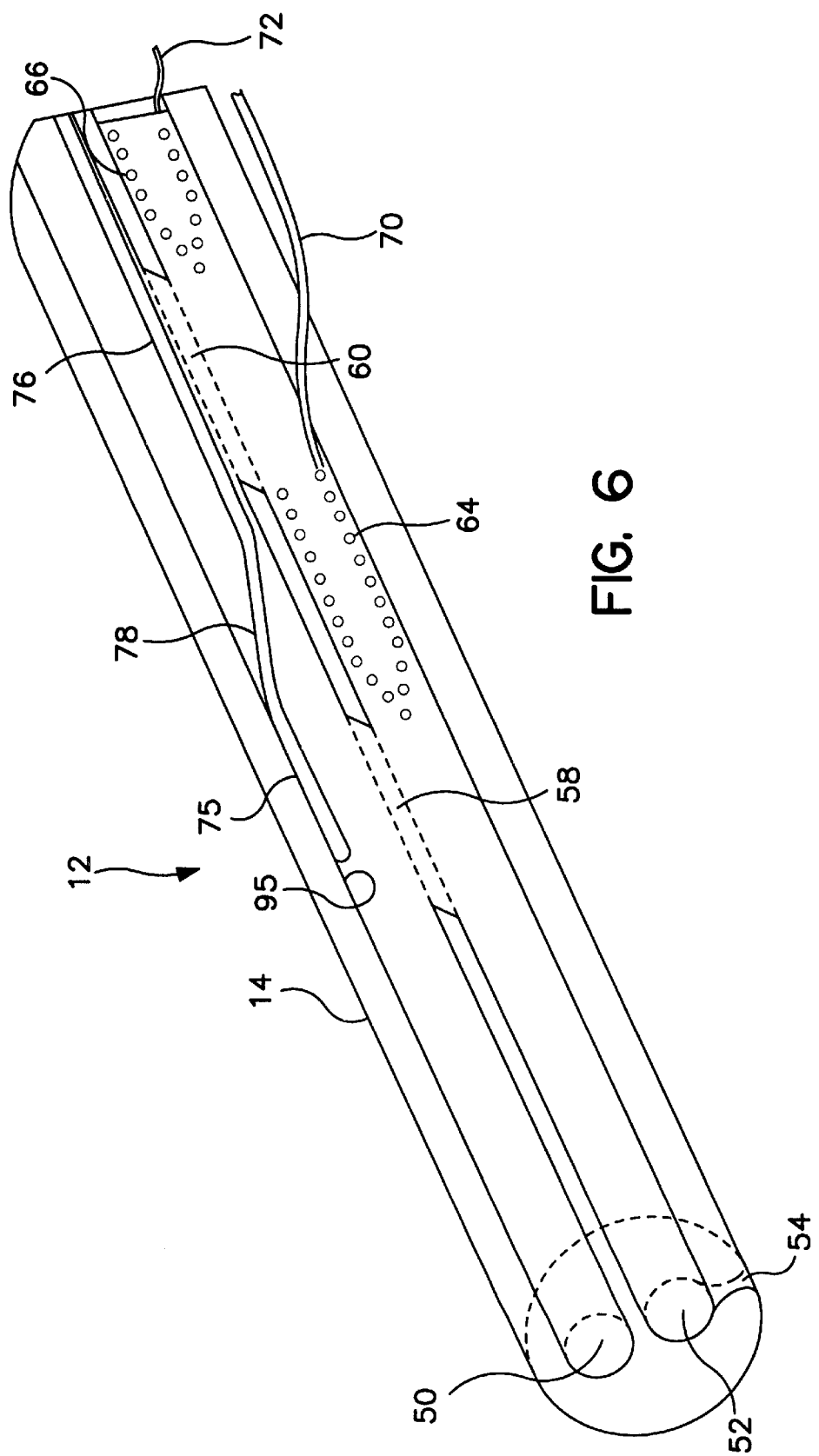
FIG. 6 is a side perspective cutaway view of distal end of introducer after the most distal electrode assembly has been deployed and the stylet has been retracted.

FIG. 6 is a side perspective cutaway view of distal end 14 of introducer 12 after electrode assembly 62 has been deployed. As discussed above, stylet 76 is pulled in the proximal direction to cause distal end 75 and canted portion 78 to enter lumen 50. When the stylet has been pulled in the proximal direction within lumen 50 a predetermined distance, a marker mechanism indicates to the user that stylet should be rotated 180 degrees. This urges distal end 75 of stylet against outer-most wall 95 of lumen in the manner shown in FIG. 6. The entire assembly, including introducer 12 and stylet 76 is then moved in a proximal direction to the next implant site. Finally distal end 75 of introducer 12 is aligned adjacent to gap 60 so that electrode assembly 64 may be deployed in the manner discussed above.

Figure 7:
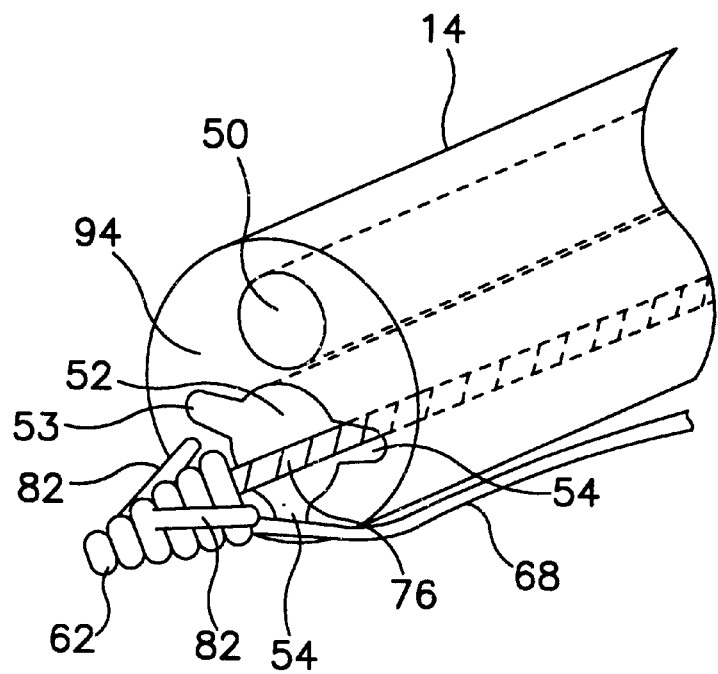
FIG. 7 is a perspective view of an exemplary electrode assembly and distal end of introducer illustrating the manner in which the electrode assembly may be deployed.

FIG. 7 is a perspective view of electrode assembly 62 and distal end 14 of introducer, and illustrates the manner in which the electrode assembly may be deployed after being pushed from channel 52 of introducer 12. This view shows an embodiment of electrode assembly 62 including expandable members 82, which unfold after electrode assembly exits channel 52. These expandable members 82 contact distal end face 94 of introducer 12 when stylet 76 is pulled in a proximal direction. This contact urges the electrode assembly from the stylet distal end 75. The use of expandable members 82 is discussed further below. According to one aspect of the invention, channel 52 may include cutaway side portions 53 and 54 to accommodate the expandable members 82 when the electrode assembly 62 resides within the channel.

Figure 8:
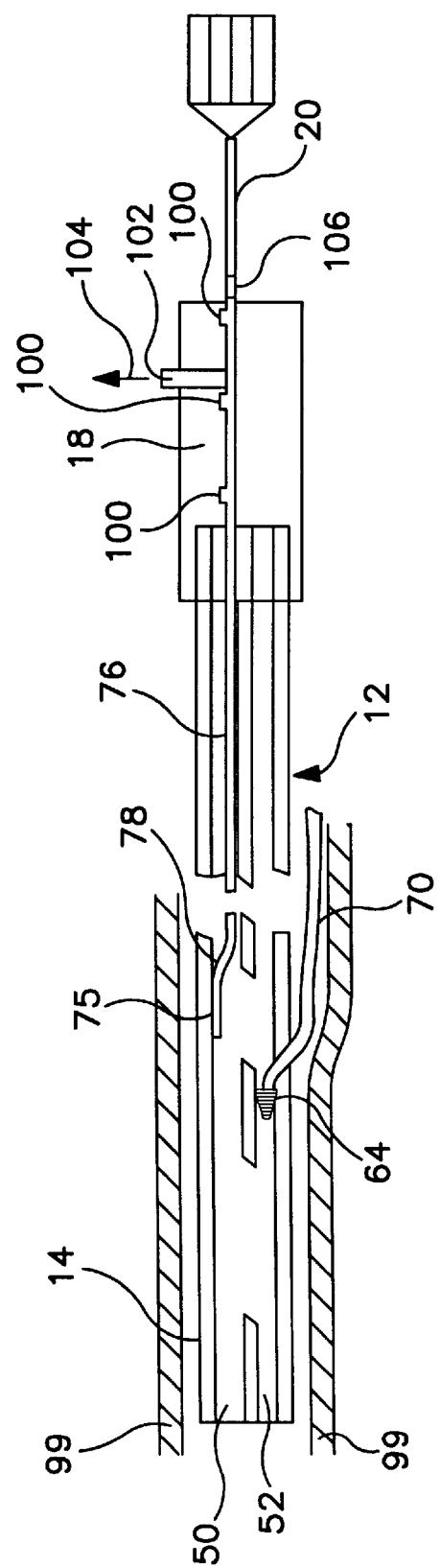
FIG. 8 is a plan view of one embodiment of the marker mechanism included within handle of introducer.

FIG. 8 is a plan view of one embodiment of the marker mechanism included within handle 18 used to retract stylet in a proximal direction during electrode deployment. In this view, distal end 14 of introducer 12 is positioned within a vessel 99. The electrode assembly 62 has already been deployed from distal end 14 of introducer 12. As discussed above, after electrode assembly 62 has been deployed, electrode assembly 64 will be deployed next. To accomplish this, distal end 75 and canted portion 78 of stylet is retracted into lumen 50 and rotated by 180 degrees. Then stylet may be pulled in the proximal direction until a marker mechanism in the handle indicates the stylet is in position to deploy the next electrode. The stylet is then rotated to engage the electrode assembly in the manner discussed above.

In the embodiment of FIG. 8, marker mechanism comprises protrusions 100 on proximal end of stylet 76. These protrusions 100 are sized to allow passage within lumen 50. However, when the stylet is pulled in a proximal direction, the protrusions collide with a spring-loaded travel limiter 102 mounted in the handle 18. This prevents further proximal motion of the stylet, and indicates to the user that the stylet is in position to deploy another electrode assembly in the manner discussed above. After deployment of electrode assembly 64, further proximal movement of the stylet is allowed by pulling spring-loaded travel limiter 102 away from handle 18 in the direction indicated by arrow 104. This allows the protrusion to pass under the travel limiter as stylet 76 is pulled in the proximal direction. The travel limiter 102 may then be released, allowing the spring-loaded mounting to return the travel limiter to a position adjacent stylet. As discussed above, in one embodiment, protrusions are positioned along stylet both to indicate when the stylet may be rotated to allow it travel within lumen 50, and also when the stylet is positioned to deploy an electrode assembly. It may be noted that protrusion of the type discussed above may be used to initially position stylet over gap 58 prior to deploying electrode assembly 62. In that instance, protrusion will collide with the proximal side of travel limiter as the stylet is being moved in a distal direction.

Various marker mechanisms may be used to facilitate the deployment of the electrode assemblies. In one embodiment, protrusions 100 are machined into stylet. In another embodiment protrusions are formed of a heat shrink tubing that is contracted to adhere to stylet 76. In this embodiment, the tubing may be removed, if desired, and repositioned to accommodate different electrode spacings. In yet another embodiment, the marker mechanism may employ visible markers such as marker 106 that may be used in place of, or in addition to, protrusions 100 by a physician during electrode deployment.

Although the above embodiment of the invention includes a marker mechanism to aid in positioning stylet 76 within lumen 50, some or all of the markers may not be needed if electrode assemblies are always to be deployed in order, starting with the most distal electrode. For example, lumen may be sized so that the distal end of lumen is positioned above gap 58. In this manner, collision of the distal end of the stylet 75 with the distal end of the lumen indicates that stylet is in positioned to deploy the most distal electrode assembly 62. After deployment of electrode assembly 62, the distal end of stylet may be pulled into lumen 50 without rotating this distal end. Pressure on the distal end resulting from canted portion 78 causes distal end to drop into gap 60 as retraction of the stylet within lumen 50 continues in a proximal direction. In this embodiment, no marker mechanism is necessary. However, this mechanism requires that electrodes are deployed in an ordered fashion, starting with the most distally-positioned electrode assembly.

Figure 9:
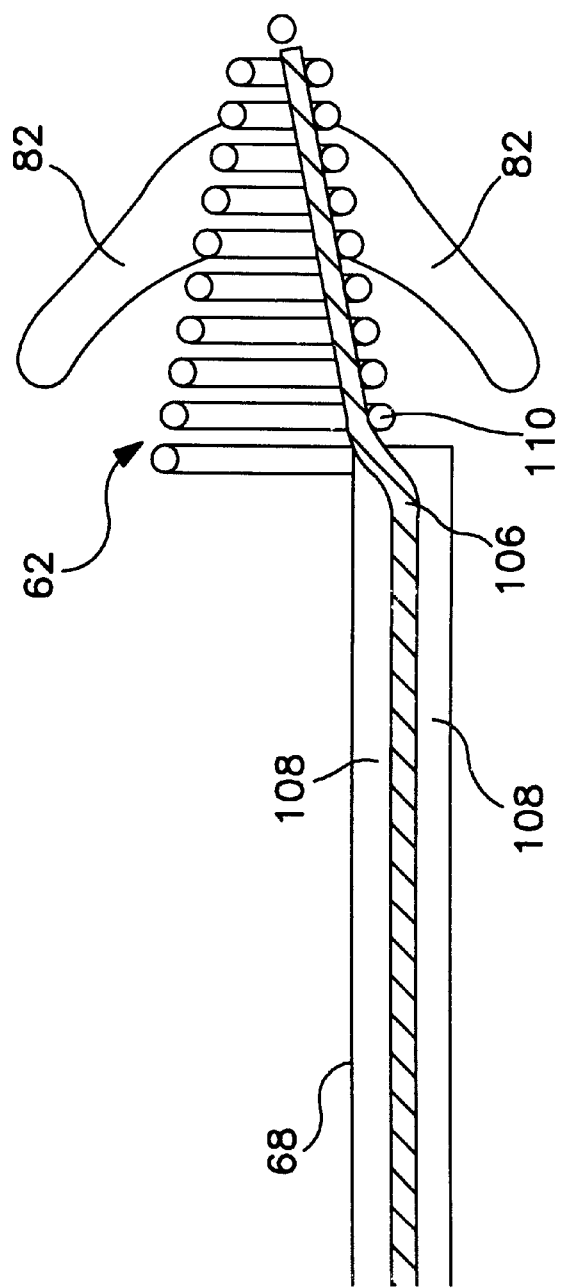
FIG. 9 is a side cutaway view of the embodiment of the electrode assembly illustrated in FIG. 3.

FIG. 9 is a side cutaway view of the embodiment of electrode assembly 62 illustrated in FIG. 3, although many other types of electrode assemblies are useful in the practice of the current invention. Electrode assembly 62 is coupled to lead body 68, which carries conductor 106. Conductor 106, which may be a coiled or stranded conductor of any of the embodiments known in the art, extends to proximal end of lead body 68 to electrically coupled electrode assembly 62 to a connector pin, as will be discussed further below. Lead body 68 further includes an insulative layer 108, which may be formed of silicone rubber, or any kind of a biostable polymer. Insulative layer 108 may include a lubricious coating of material such as Teflon to aid in deploying the lead from channel 52.

Conductor 106 is electrically coupled to a second coil conductor 110, that may be a loosely-wound coil as illustrated in FIG. 9, or may be more tightly wound. Conductor 106 may be soldered, welded, crimped, brazed, or otherwise joined to coil conductor 110 to produce both a mechanical and electrical connection. In one embodiment, distal end of conductor 106 is shaped to form conical? coiled conductor 110 so that no mechanical coupling is required. According to one aspect of the invention, coil may be coated with a material such as expanded Polytetrafluoroethylene (e-PTFE) to prevent tissue in-growth around the coil structure while selectively allowing tissue in-growth at predetermined portions of the lead. This is described further in U.S. patent application filed on even date herewith entitled "Implantable Medical Electrical Lead" which is incorporated herein by reference in its entirety.

The electrode assembly includes expandable members 82, such as is shown in FIG. 7. In this embodiment, expandable members 82 are pliant tines that may be formed of a flexible silicone rubber, a polymer such as a polyurethane, or a shape memory alloy such as superelastic Nitinol. It may be noted that if the electrode assembly is to be pre-loaded within channel 52 for a long period of time such as during the shelf-life of the product, use of a material such as Nitinol to form the tines is preferred, since this type of material will not become set in a contracted position.

The tines may be folded around a portion of coiled conductor 110 before the electrode assembly is inserted within channel 52. In this manner, tines 82 do not interfere with, or impede, deployment of the electrode assembly. As mentioned above, cutaway portions such as shown in FIG. 7 may be provided in channel 52 to further reduce friction resulting from the tines. However, once the lead is properly positioned within an artery or vein, the tines expand to engage the inner wall of the artery or vein. This retains the electrode assembly 62 at a desired implant site until growth of fibrotic tissue begins, which aids in holding the electrode assembly in place.

In one embodiment, coiled conductor may be partially coated with an insulating material so that a predetermined amount of current flow between the electrode assembly and tissue occurs. This allows cardiac tissue depolarization to be optimized in a manner known in the art.

Figure 10:
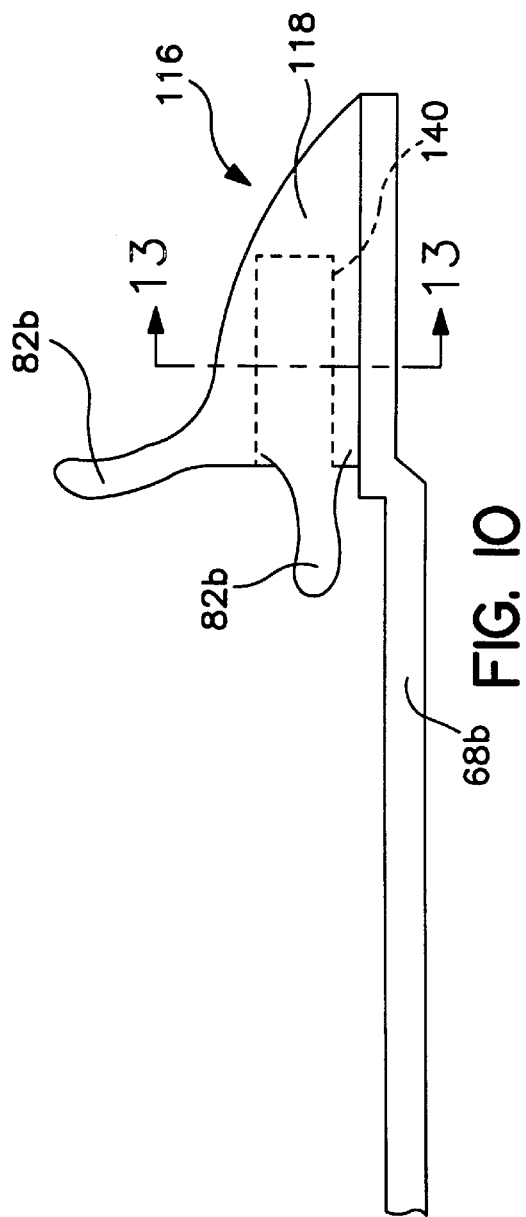
FIG. 10 is a plan view of another embodiment of an electrode assembly that may be used in conjunction with the current invention.

FIG. 10 is a plan view of another embodiment of an electrode assembly that may be used in conjunction with the current invention. This electrode assembly 116 has a generally tubular body 118 mounted on lead body 68b. Lead body may be of any of the configurations discussed above in reference to FIG. 9. A conductor (not shown) carried by lead body is electrically coupled to tubular body, which may be comprised of platinum-iridium alloy with a sintered and platinized surface. Affixed to tubular body are multiple pliant tines 82b similar to those discussed above in reference to FIG. 9, and which are employed to maintain the lead at a desired implant site until tissue in-growth begins. In one embodiment, tubular body 118 includes a keyed slot 140 (shown dashed) used to engage a stylet during electrode deployment in a manner to be discussed further below.

FIG. 11 is a plan view of yet another embodiment of an expandable electrode assembly. A structure similar to the electrode assembly is shown and described in U.S. Pat. No. 5,071,407 incorporated herein by reference. In this embodiment, electrode assembly comprises two collars 120 and 122 coupled to a basket-like, open weave, structure 124. One or more of collars 120 and 122 is capable of engaging stylet 76 during the deployment of the electrode assembly in a manner to be discussed below.

The basket-like structure is formed of braided, elastic material. Similar structures are commercially available for use as vena cava filters. When opposing forces are applied to collars 120 and 122, electrode assembly assumes an elongated configuration with a reduced diameter that is sized to fit within channel 52. After being deployed however, structure 124 assumes an expanded-diameter configuration that contacts adjacent tissue of a vessel to retain the electrode at a predetermined implant site. Basket-like structure 124 is formed, at least in part, of conductive strands such as filaments of resilient stainless steal that are electrically coupled to a conductor carried by lead 126 (not shown), which may be of any of the lead configurations discussed above. Thus, at least a portion of the structure 124 is capable of delivering electrical stimulation to a vessel.

FIG. 12 is a plan view of the electrode assembly embodiment of FIG. 11 within a vessel 130 after the electrode has been deployed, and has assumed a self-expanded configuration.

Returning now to FIG. 10, one manner of engaging an electrode assembly with a stylet is discussed.

Figure 13:
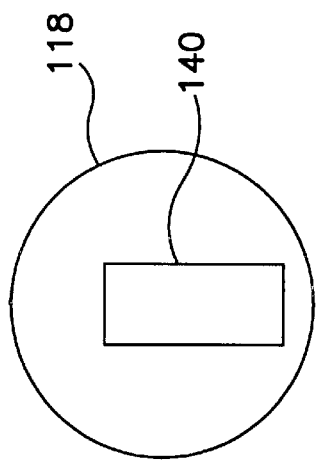
FIG. 13 is a cross-sectional view of the electrode assembly of FIG. 10 at line 13—13 showing a keyed channel to engage a bladed stylet.

FIG. 13 is a cross-sectional view of one embodiment of the electrode assembly of FIG. 10 at line 13—13. This view shows a keyed slot 140 within tubular body 118 to receive a slotted end of a stylet. For example, slot 140 may be adapted to receive the bladed end of a stylet in a manner discussed in provisionally-filed U.S. Patent Application Serial No. 60/257,459 filed Dec. 21, 2000 entitled "Medical Electrical Lead Having An Expandable Electrode Assembly", which is incorporated herein by reference in its entirety.

Figure 14:
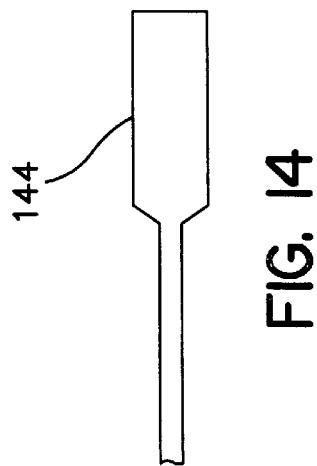
FIG. 14 is a plan view of a stylet having a bladed distal end, as may be used to deploy an electrode of the type discussed in FIGS. 10 and 13.

FIG. 14 is a plan view of a stylet having a bladed distal end 144, as may be used to deploy an electrode of the type discussed in FIGS. 10 and 13. It may be noted that any of the electrodes discussed with respect to the current invention may include a keyed member such as slot 140 adapted to engage a stylet in the manner discussed above. For example, one or both of collars 120 and 122 of the electrode assembly of FIG. 11 may include a keyed structure, as may the electrode of FIG. 9. Such a keyed structure aids in rotating an electrode assembly upon deployment. A keyed structure also aids in repositioning electrode assembly after it is initially positioned within a vessel.

FIG. 7 is a perspective view of electrode assembly 62 and distal end 14 of introducer, and illustrates the manner in which the electrode assembly may be deployed after being pushed from channel 52 of introducer 12. This view shows an embodiment of electrode assembly 62 including expandable members 82, which unfold after electrode assembly exits channel 52. These expandable members 82 contact distal end face 94 of introducer 12 when stylet 76 is pulled in a proximal direction. This contact urges the electrode assembly from the stylet distal end 75. The use of expandable members 82 is discussed further below. According to one aspect of the invention, channel 52 may include cutaway side portions 53 and 54 to accommodate the expandable members 82 when the electrode assembly 62 resides within the channel.

Figure 15A:
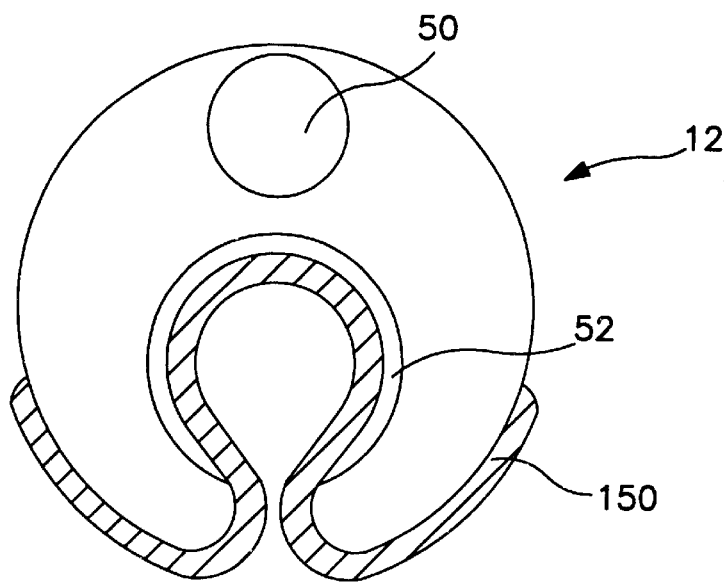
FIG. 15A is a cross-sectional view of yet another embodiment of an expandable electrode assembly suitable for use with the current invention.

FIG. 15A is a cross-sectional view of yet another embodiment of an expandable electrode assembly suitable for use with the current invention. Electrode assembly 150, which may be formed of a deformable superelastic alloy such as Nitinol, is shown loaded into channel 52 of introducer 12.

Figure 15B:
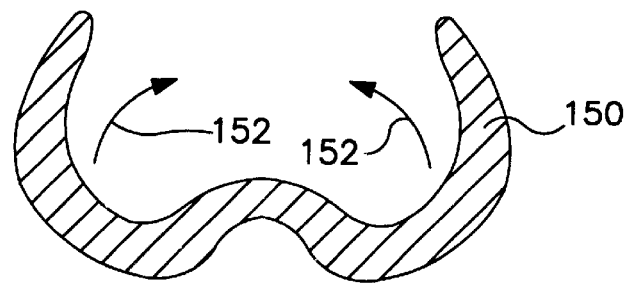
FIG. 15B is a cross-sectional view of the electrode assembly of FIG. 15A just after it is deployed from an introducer.

FIG. 15B is a cross-sectional view of the electrode assembly 150 of FIG. 15A just after it is deployed from introducer 12. The electrode assembly begins to assume a trained shape, as shown by arrows 152.

Figure 15C:
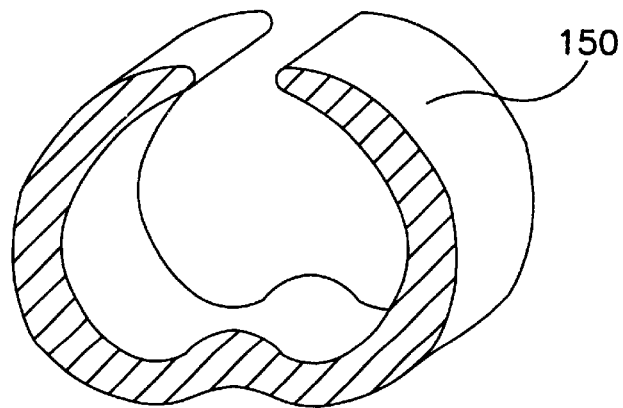
FIG. 15C is a perspective view of the electrode assembly of FIG. 15A after it has assumed a trained shape.

FIG. 15C is a perspective view of the electrode assembly 150 of FIG. 15A after it has assumed its generally tubular, trained shape. This embodiment has the advantage of providing a relatively large, deployed electrode configuration that may be loaded into a much smaller introducer channel. Thus, the overall dimensions of the introducer can be made smaller while still retaining adequate electrode characteristics.

It will be understood by one skilled in the art that other electrode configurations may be used with the current invention. For example, the electrode configurations disclosed in provisionally-filed U.S. Patent Application Serial No. 60/257,459 referenced above are readily adaptable for use with the current inventive system.

FIG. 16 is a plan view illustrating one embodiment of electrode assemblies 62, 64, and 66 configured to interconnect to a single connector pin. In this embodiment, the conductors carried by the respective leads 68, 70 and 72 discussed above are electrically coupled in this embodiment at connector assembly 160. A common conductor extending from connector assembly 160 to connector pin 162 electrically couples all of the electrodes to the connector pin. Connector pin 162 may be configured according to any connector standard used for implantable devices, such as the low profile connector "IS-1" standard (ISO 5841-3:1992(E)) for bipolar in-line and unipolar lead connector end assemblies. Other permanent, bipolar, in-line, cardiac lead connector end assemblies conform dimensionally with the 3.2 mm low profile connector standard leads commercially available from the Medtronic Corporation. Certain permanent unipolar cardiac lead connector end assemblies conform dimensionally with the Medtronic Corporation 5 mm connector standard.

In use, the current invention may be guided to a desired implant site using a guide catheter of any type known in the art. For example, a guide catheter may be advanced within the coronary sinus, and if desired, into one of the branch veins. The introducer 12, which is pre-loaded with a predetermined number of electrode assemblies, is then advanced within an inner lumen of the guide catheter. The guide catheter may then be withdrawn and the electrode assemblies placed in accordance with the above described method. Many types of guide catheters may be used for this purpose, including the ZUMA® guide catheters commercially available from Medtronic, Inc. Other exemplary structures of similar catheters are disclosed in U.S. Pat. No. 5,755,704 issued to Lunn, U.S. Pat. No. 5,545,149, issued to Brin, et al. and U.S. Pat. No. 5,811,043 issued to Horrigan, et al.

In an alternative method of use, a guidewire may be used to navigate introducer to a desired site of implant. The guidewire is first positioned in the coronary sinus or branch vein. Then open lumen 50 of introducer may be advanced over a guide wire. Guidewire is retracted prior to inserted canted stylet 76 into lumen 50 to deploy the electrode assemblies in the manner discussed above.

As discussed above, the current invention is particularly adapted for placing an array of defibrillation electrodes within the coronary sinus or a branch vein. For example, a guide catheter may be advanced through the coronary sinus ostium. The electrode assemblies may then be deployed within the coronary sinus, or a canted stylet such as stylet 76 of FIG. 2 may be advanced outside of channel 52 and guided into a branch vein to place one or more of the electrodes within the branch vein.

Figure 17:
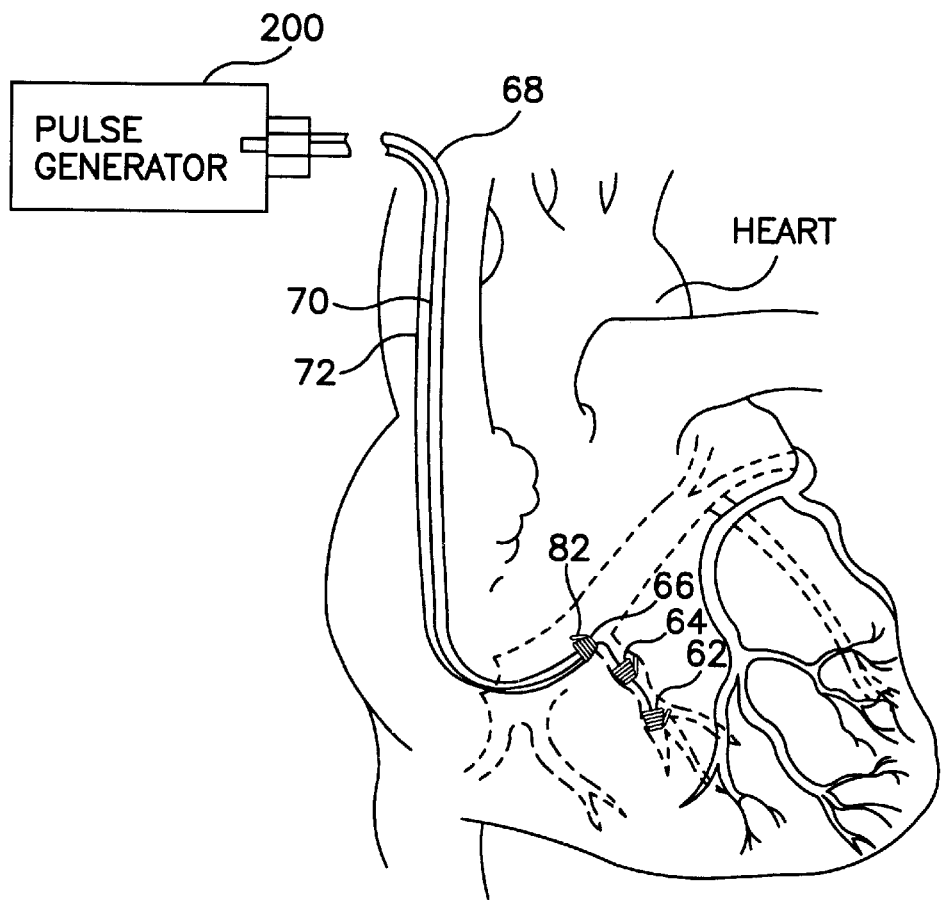
FIG. 17 is a diagram of a human heart illustrating an exemplary embodiment of the current inventive lead system placed within a branch vein of the coronary sinus.

FIG. 17 is a diagram of a human heart illustrating three electrode assemblies placed within the vascular system of a human heart. Electrode assemblies 62 and 64 are shown positioned within the Middle Cardiac Vein (MCV), a branch vein of the coronary sinus, as may be accomplished using stylet. Electrode 66 is placed within the coronary sinus, and maintained in place by explandable members 82. If desired, all electrode assemblies could be placed within the same branch vein such as the MCV or a different vein. Alternatively, all electrode assemblies may be placed within the coronary sinus using the current invention system and method.

The electrode assemblies are coupled to a respective one of leads 68, 70, and 72, which extend through the ostium of the coronary sinus or the middle cardiac vein, through the right atrium and into the superior vena cava. These leads extend to pulse generator 200, which may be implanted under the skin and muscle tissue of the upper chest in a manner known in the art.

According to one embodiment of the invention, the lead assembly further includes a mechanism to maintain the leads in a relative location with respect to one another after all electrode assemblies are deployed. This minimizes wear on the leads, and further prevents irritation cause by the multiple leads rubbing against tissue.

Figure 18:
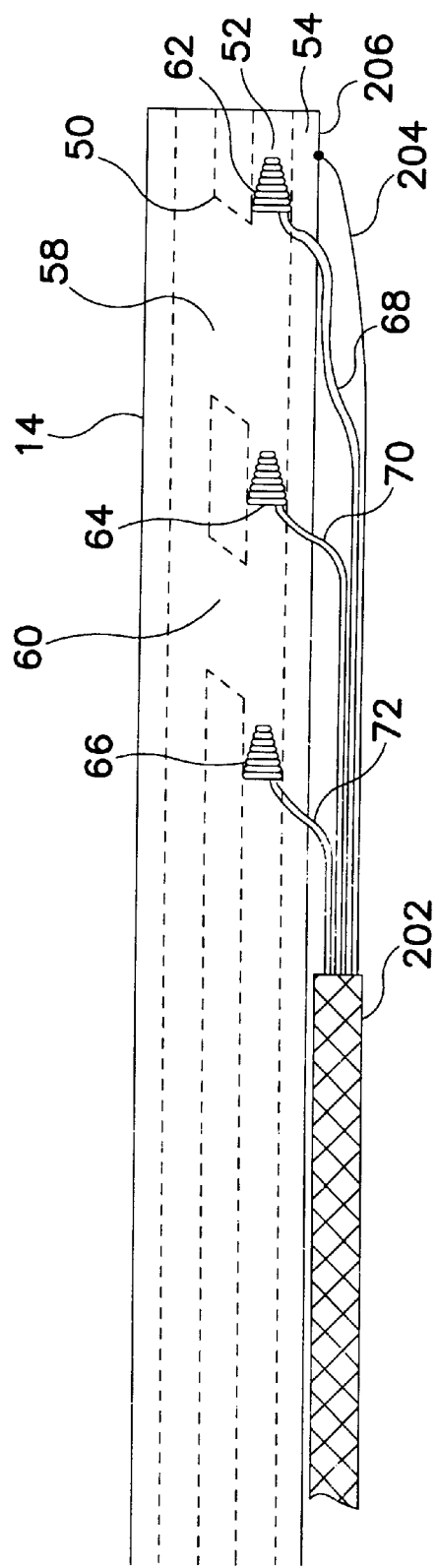
FIG. 18 is a side cutaway view of the inventive system illustrating one embodiment of a mechanism to maintain the leads in a stationary position relative to one another.

FIG. 18 is a side cutaway view of the inventive system illustrating one embodiment of a mechanism to maintain the leads in a stationary position relative to one another. This figure shows the electrodes positioned within distal end 14 of introducer 12. The leads 68, 72, and 74 are enclosed within a loosely braided sheath or tube 202 woven of fibers that may be made of a lubricious material such as PTFE or ETFE. The tube 202 lies adjacent to, and extends to proximal end of, introducer 12. During the implant procedure, proximal end of tube 202 lies outside of the body. Tube 202 is anchored to distal end 14 of introducer with a flexible tether 204, as may be made of silicon rubber or a surgical Dacron suture material. The tether incorporates a slip knot 206. After all of the electrode assemblies are placed, the proximal end of tube 202 may be pulled tight so that all leads are snugly bound. The length of tube 202 may extend distally so that leads are bound up to the point of exiting a branch vein such as the MCV. By incorporating a weakened spot in the tether 204, the tether may be disconnected from introducer after adequate tension is applied at the distal end.

The manufacture of the current inventive system can be performed by molding or extruding introducer to include slot 54, channel 52, and lumen 50. Alternatively, two lumens may be formed to extend through the length of the introducer and through the introducer distal end. Then portions of the introducer may be cut away to form slot 54 and channel 52 from a first lumen, and to further form gaps 58 and 60 at predetermined locations. The electrodes are then pre-loaded through slot 54 into channel 52 at predetermined locations distal to a respective gap. In one embodiment, the leads of the electrodes may be fed through a flexible sheath that is positioned outside of, and adjacent to, introducer 12, and which is attached to the distal end of introducer via a tether in a manner discussed above.

Variations and modifications to the present invention may be possible given the above disclosure. For example, although the foregoing description discusses utilizing introducer 12 to place three electrode assemblies within a patient's vascular system, it will be understood that the introducer may be adapted to implant fewer than, or more than, three electrodes. All such variations and modifications are intended to be within the scope of the invention claimed by this letters patent.

In conjunction with the above disclosure, we claim:

1. An electrode assembly system, comprising:
   an elongated member including a first lumen forming a cutaway portion and a second lumen substantially parallel to the first lumen, the first lumen in fluid communication with an external surface of the elongated member via the cutaway portion; and
   a plurality of electrode assemblies positioned within the first lumen, wherein the first lumen and the second lumen form one or more apertures, the first lumen being in fluid communication with the second lumen via the one or more apertures.

2. The electrode assembly system of claim 1, further comprising a stiffening member inserted within the second lumen.

3. The electrode assembly system of claim 2, wherein the stiffening member includes marker means for enabling the stiffening member to be positioned at one or more predetermined locations within the second lumen.

4. The electrode assembly system of claim 2, wherein the stiffening member is a canted stylet adapted to be advanced within the first lumen from the second lumen through the one or more apertures to engage the plurality of electrode assemblies and advance the plurality of electrode assemblies through the first lumen and outward from a distal end of the elongated member.

5. The electrode assembly system of claim 4, wherein the canted stylet includes a keyed structure to engage the plurality of electrode assemblies.

6. The electrode assembly system of claim 4, wherein one of the plurality of electrode assemblies includes an expandable member adapted to expand after being advanced outward from the distal end of the elongated member.

7. The electrode assembly system of claim 6, wherein the expandable member is an expandable tine.

8. The electrode assembly system of claim 6, wherein the expandable member is an expandable braided structure.

9. The electrode assembly system of claim 6, wherein the expandable member is a deformable, substantially tubular structure.

10. The electrode assembly system of claim 4, further comprising:
   a plurality of lead bodies;
   a plurality of conductors, each of the plurality of conductors positioned within a corresponding one of the plurality of lead bodies and coupling an electrode assembly of the plurality of electrode assemblies to a proximal end of the corresponding one of the plurality of lead bodies;
   a connector pin positioned proximally from the plurality of lead bodies;
   a connector assembly positioned distally from the connector pin; and
   a common conductor extending from the connector pin to the connector assembly and electrically coupling the plurality of conductors to the connector pin, wherein the stiffening member is extended outside and along the connector assembly and the plurality of lead bodies to engage the plurality of electrodes during advancing of the plurality of electrode assemblies via the stiffening member.

11. The electrode assembly system of claim 10, wherein the plurality of electrode assemblies include a first electrode electrically coupled to a first conductor of the plurality of conductors and a second electrode electrically coupled to a second conductor of the plurality of conductors, and wherein the stiffening member is advanced to the first conductor to deploy the first electrode along a first site of the multiple sites and to the second conductor to deploy the second conductor along a second site of the multiple sites different from the first site while the first conductor is deployed along the first site.

12. The electrode assembly system of claim 11, wherein the first conductor has a first conductor length and the second conductor has a second conductor length greater than the first conductor length.

13. The electrode assembly system of claim 4, wherein the plurality of electrode assemblies include a slotted portion receiving the stiffening member during the advancing of the plurality of electrode assemblies via the stiffening member.

14. The electrode assembly system of claim 4, wherein the plurality of electrode assemblies assume a first shape, corresponding to the elongated member, prior to the advancing of the plurality of electrode assemblies and a second shape subsequent to the advancing of the plurality of electrode assemblies.

15. The electrode assembly system of claim 4, wherein the plurality of electrode assemblies assume a first non-tubular shape immediately following the advancing of the plurality of electrode assemblies outward from the distal end of the elongated member and a generally tubular shape subsequent to assuming the non-tubular shape.

16. The electrode assembly system of claim 4, wherein an electrode assembly of the plurality of electrode assemblies is an expandable electrode.

17. The electrode assembly system of claim 16, wherein the electrode assembly of the plurality of electrode assemblies includes a collar engaging the stiffening member during deployment.

18. The electrode assembly system of claim 16, further comprising:
   a plurality of lead bodies; and
   a plurality of conductors, each of the plurality of conductors positioned within a corresponding one of the plurality of lead bodies and coupling an electrode assembly of the plurality of electrode assemblies to a proximal end of the corresponding one of the plurality of lead bodies, wherein the electrode assembly of the plurality of electrode assemblies is formed of a braided elastic material and includes conductive strands electrically coupled to a corresponding conductor of the plurality of conductors.

19. The electrode assembly system of claim 1, further comprising an inflation member adapted to temporarily retain the elongated member at a predetermined location within a body.

20. The electrode assembly system of claim 1, further comprising a plurality of lead bodies, wherein each of the plurality of electrode assemblies is coupled to a lead body of the plurality of lead bodies extending through the cutaway portion and positioned adjacent the external surface of the elongated member.

21. The electrode assembly system of claim 20, further comprising a sheath surrounding ones of the plurality of lead bodies.

22. The electrode assembly system of claim 21, wherein the sheath includes a tether to the elongated member.

23. The electrode assembly system of claim 1, wherein the one or more electrode assemblies are formed from a deformable superelastic alloy.

24. The electrode assembly system of claim 23, wherein the deformable superelastic alloy is Nitonal.

* * * * *